United States Patent [19]

Igarashi et al.

[11] Patent Number: 5,105,091
[45] Date of Patent: Apr. 14, 1992

[54] NON-CONTACT TYPE AUTOMATIC MULTI-POINT DIAMETER MEASUREMENT APPARATUS

[75] Inventors: Kazuhiko Igarashi; Masami Takahashi, both of Fukushima, Japan

[73] Assignee: Shin-Etsu Handotai Co., Ltd., Tokyo, Japan

[21] Appl. No.: 538,342

[22] Filed: Jun. 13, 1990

[30] Foreign Application Priority Data

Jun. 21, 1989 [JP] Japan .................. 1-71659[U]

[51] Int. Cl.$^5$ .............................................. G01N 21/86
[52] U.S. Cl. ...................................... 250/560; 356/386
[58] Field of Search ............... 250/560, 571; 356/385, 356/386, 387

[56] References Cited

U.S. PATENT DOCUMENTS

| | | | |
|---|---|---|---|
| 3,724,958 | 4/1973 | Callan | 250/560 |
| 4,260,260 | 4/1981 | Letort et al. | 356/385 |
| 4,416,541 | 11/1983 | Studer | 356/385 |
| 4,657,395 | 4/1987 | Schiraishi et al. | 356/385 |
| 4,912,337 | 3/1990 | Wilwerding | 250/560 |

Primary Examiner—David C. Nelms
Assistant Examiner—K. Shami
Attorney, Agent, or Firm—Lowe, Price, LeBlanc & Becker

[57] ABSTRACT

A non-contact type automatic multi-point diameter measurement apparatus for measuring diameters of a single crystal ingot pulled up in a single crystal pulling apparatus, adapted to measure the diameters in a real time manner without physically coming in contact with the single crystal ingot, comprising: a light emitter having a length substantially greater than the general diameter of the single crystal ingot and adapted to shift in the direction of the axis of the single crystal ingot; an optical diameter measurement device looking toward the light emitter across the single crystal ingot, adapted to shift together with the light emitter so as to always look toward the light emitter across the single crystal ingot, located at such a predetermined position relative to the light emitter and the single crystal ingot that at least the light emitted from both ends of the light emitter can reach the optical diameter measurement device without being intercepted by the single crystal ingot, and adapted to optically measure a diameter of the single crystal ingot; a position detection device for detecting whether the optical diameter measurement device is in one of predetermined positions; a control device for actuating the optical diameter measurement device to measure a diameter of the single crystal ingot; and a data processing device for calculating a representative value of the diameter values based on the measurement result diameters.

6 Claims, 3 Drawing Sheets

NON-CONTACT TYPE AUTOMATIC MULTI-POINT DIAMETER MEASUREMENT APPARATUS

BACKGROUND OF THE INVENTION

1. Field of the Invention

The present invention relates to a non-contact type automatic multi-point diameter measurement apparatus capable of continuously measuring the diameter of a cylindrical work with high precision at a plurality of locations along the axis of the work in a real time manner.

2. Background of the Prior Art

Various devices are known for the measurement of diameters. For example, in the semiconductor manufacturing process, diameters of an as-grown single crystal ingot pulled up in a single crystal pulling apparatus were conventionally measured with calipers applied to different locations along the axis of the ingot.

In a single crystal pulling apparatus, the diameter of a single crystal ingot being pulled up is optically detected by means of an image sensor, and the accuracy of this image sensor is maintained by the adjustment thereof (such as zero point calibration in voltage) based on the actual diameter data (measured by the calipers) of the single crystal ingot which are supplied to the single crystal pulling apparatus in a feedback manner.

However, with the conventional manual measurement method, the result of the measurement is not free of the individual measurer's errors in determining the value, so that it is difficult to obtain reliable data with high precision. Furthermore, since the time efficiency of the measurement is not high due to the manual nature of the measurement, it is difficult to take diameters at a sufficient number of positions along the axis of the work (ingot), and, as a result, the data obtained are liable to be too insufficient to enable minute comparison between the actually measured values of the diameters (the diameters measured with calipers) and the diameter values detected by the image sensor of the single crystal pulling apparatus, so that an accurate determination of the errors in the latter values is difficult, and thus it is impossible to conduct a reliable adjustment of the accuracy of the image sensor, and, hence, it is impossible to attain high precision controlling of the diameter of the single crystal ingot grown in the single crystal pulling apparatus.

SUMMARY OF THE INVENTION

The present invention was contrived in view of the above problems, and, therefore, it is an object of the invention to provide a non-contact type automatic multi-point diameter measurement apparatus which can continuously measure the diameter of a cylindrical work with high precision at a plurality of locations along the axis of the work in a real time manner.

In order to achieve the above object and others, the present invention proposes a non-contact type automatic multi-point diameter measurement apparatus for measuring diameters of a cylindrical body in a real time manner without physically coming in contact with the cylindrical body, characterized by comprising:

an elongated light emitting means having a length substantially greater than the general diameter of the cylindrical body and adapted to shift in the direction of the axis of the cylindrical body which is generally normal to the lengthwise axis of the light emitting means;

an optical diameter measurement means looking toward the light emitting means across the cylindrical body, adapted to shift together with the light emitting means so as to always look toward the light emitting means across the cylindrical body, located at such a predetermined position relative to the light emitting means and the cylindrical body that at least the light emitted from both ends of the light emitting means can reach the optical diameter measurement means without being intercepted (eclipsed) by the cylindrical body, and adapted to optically measure a diameter of the cylindrical body and output a signal indicative of the result of the diameter measurement;

a position detection means for detecting whether the optical diameter measurement means is in one of predetermined positions, and outputting a detection signal when it is detected that the optical diameter measurement means is in one of the predetermined positions;

a control means for actuating the optical diameter measurement means to measure a diameter of the cylindrical body in response to the detection signal received from the position detection means; and a data processing means for calculating a representative value of the diameter values based on the measurement result signal received from the optical diameter measurement means, and processing the resulting data of diameters.

In a preferred embodiment of the invention, the elongated light emitting means is covered with a cover means having a slit extending along the length of the light emitting means which slit is substantially longer than the general diameter of the cylindrical body, and the optical diameter measurement means is located at such a predetermined position relative to the slit and the cylindrical body that at least the light emitted through both end portions of the slit can reach the optical diameter measurement means without being intercepted by the cylindrical body.

In another preferred embodiment of the invention, the optical diameter measurement means includes an image sensor.

In a still other preferred embodiment of the invention, the light emitting means comprises a high-frequency fluorescent lamp.

According to the present invention, as the optical diameter measurement means is shifted in the direction of the axis of the cylindrical body (work), the position detection means detects whether the optical diameter measurement means has arrived in any of the predetermined positions, and each time the optical diameter measurement means has arrived in any of the predetermined positions, the position detection means generates a detection signal to thereby cause the control means to actuate the optical diameter measurement means to measure a diameter of the cylindrical body, and accordingly it is possible to measure the diameters of the cylindrical body at more than one point along the axis of the cylindrical body in a real time manner, and the signals representing the results of the diameter measurement are sent to the data processing means for calculating the value of a diameter based on the measurement result signal received from the optical diameter measurement means, where the representative value of actually measured diameter values is determined and stored. As described above, with the apparatus of the present invention, there is no step whereat any human judgment is required, so that the measured diameter values are free of errors ascribable to human inconsistency, and thus reliable data are constantly obtained.

Also, since the number of diameter measurement points along the axis of the cylindrical body can be arbitrarily determined, it is possible to secure a sufficient amount of measurement data. Thus, in the above embodiment, for example, the data of the actually measured values of diameters stored in the data processing means are outputted as reference data, and with them the diameter detection data obtained by means of the image sensor of the single crystal pulling apparatus are compared, and based on the result of the comparison the degradation in the accuracy of the image sensor is corrected, whereby it is possible to conduct the diameter control of the as-grown ingot being pulled up in the single crystal pulling apparatus with higher precision.

BRIEF DESCRIPTION OF THE DRAWINGS

An embodiment of the invention will be described with reference to the following drawings attached hereto.

DETAILED DESCRIPTION OF THE PREFERRED EMBODIMENTS

Figure 1:
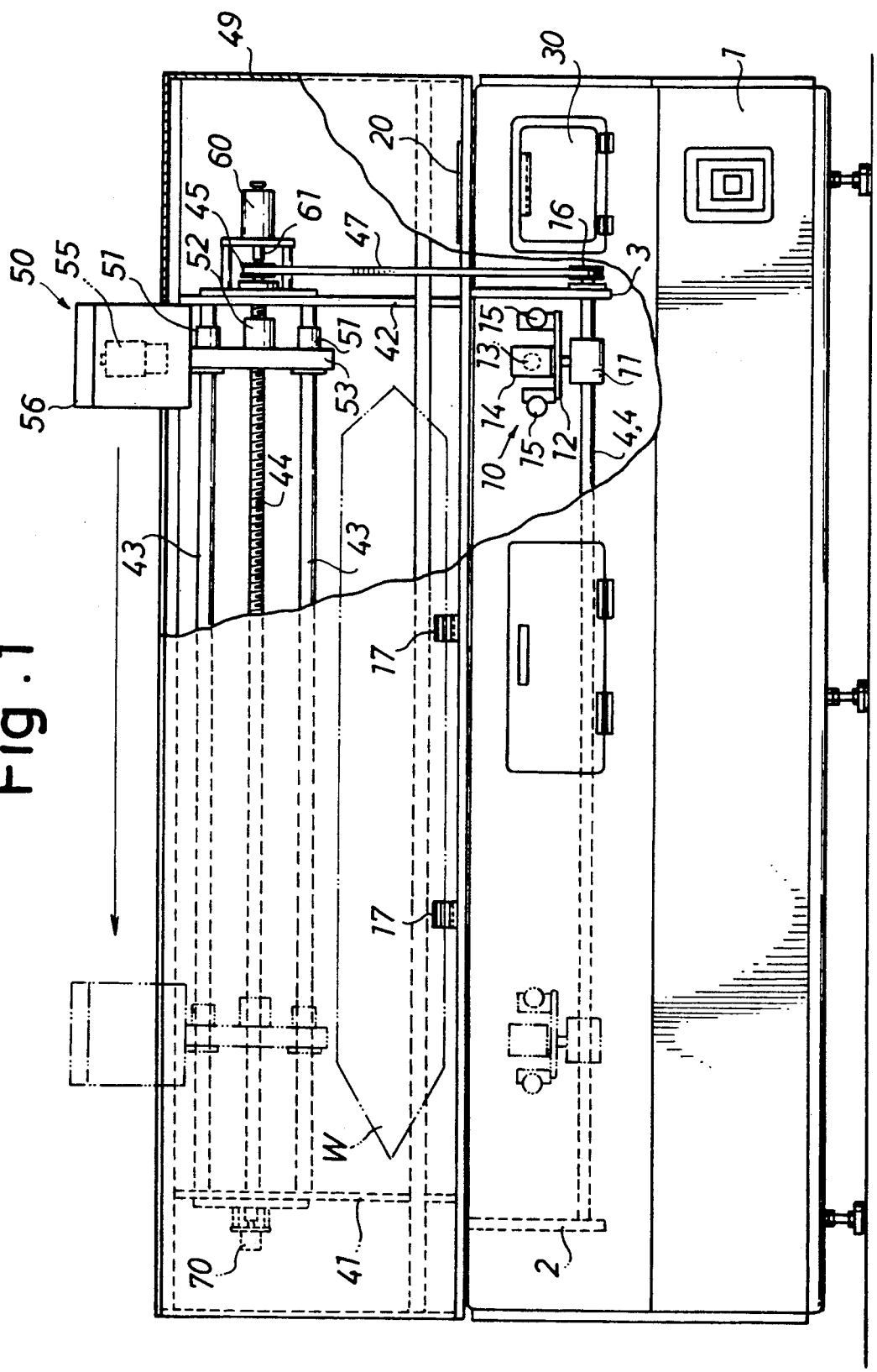
FIG. 1 is a front elevation view, partly in section, of a non-contact type automatic multi-point diameter measurement apparatus according to to the invention.
Figure 2:
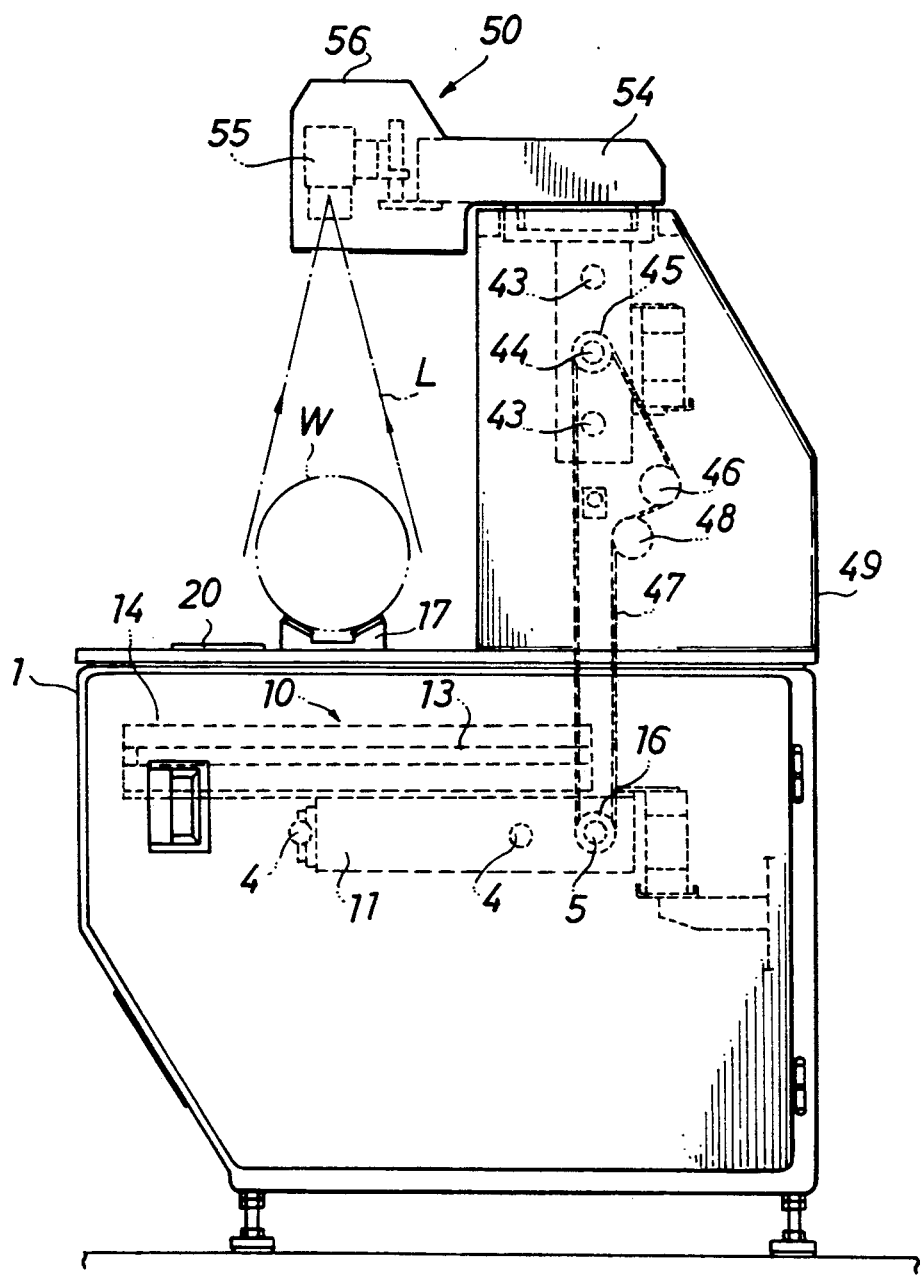
FIG. 2 is a side view of the same apparatus.

In FIG. 1 and FIG. 2, the reference numeral 1 designates a base box. Inside the base box 1, vertical support plates 2 and 3 are fixedly suspended from the ceiling of the base box 1, in a manner such that the support plates are both normal to the plane of the sheet of FIG. 1 and at a predetermined distance from each other. Two horizontal guide shafts 4, 4 and a horizontal ball screw shaft 5 are provided between, and supported by, the support plates 2 and 3, to which all shafts 4, 4, and 5 are normal. A light emission assembly 10 is supported by the guide shafts 4, 4 and the ball screw shaft 5 in a manner such that the emission assembly 10 is capable of shifting along the guide shafts 4, 4. More particularly describing, the light emission assembly 10 has a slider 11 on which the rest of the light emission assembly 10 is mounted, and this slider 11 is adapted to slide on the guide shafts 4, 4 and is threadably penetrated by the ball screw shaft 5 so that that as the ball screw shaft 5 turns, the light emission assembly 10 is caused to shift in the direction normal to the plane of the sheet of FIG. 2. A support plate 12 is provided over the slider 11, and a high-frequency fluorescent lamp 13 housed in a cover 14 is mounted on the support plate 12. The lamp 13 and the cover 14 are elongated in the direction normal to the plane of the sheet of FIG. 1. A slit, not shown, is made in the ceiling of the cover 14 extending along the length of the cover 14. A pair of dials 15, 15 are provided on the support plate 12 which are adapted, by turning, to arbitrarily adjust the width of the slit. Incidentally, the light emission assembly 10 has a length which is large enough to enable an optical diameter measurement assembly 50 (described hereinafter) to detect at least the both ends of the light emission assembly 10.

The ball screw shaft 5 has its end portions journalled in the support plates 2 and 3 by means of bearings, not shown, and the right end, as viewed in FIG. 1, of the ball screw shaft 5 extends beyond the support plate 3 and carries a fixed pulley 16 about it.

A pair of support blocks 17, 17, set apart from each other by a predetermined distance in the direction normal to the plane of the sheet of FIG. 2, are fixedly mounted on the base box 1 for supporting horizontally a single crystal ingot W (as-grown crystal ingot) which was pulled up in a single crystal pulling apparatus, not shown. An operation panel 20 is provided on and toward the right end, as viewed in FIG. 1, of the base box 1. A controller 30 is provided on and toward the right end, as viewed in FIG. 1, of the front face of the base box 1.

Vertical support plates 41 and 42 are fixedly erected on the base box 1, in a manner such that the support plates 41 and 42 are both normal to the plane of the sheet of FIG. 1. Two horizontal guide shafts 43, 43 and a horizontal ball screw shaft 44, which is between the upper and lower guide shafts 43, 43, are provided between, and supported by, the support plates 41 and 42, to which all shafts 43, 43, and 44 are normal. The optical diameter measurement assembly 50 is supported by the guide shafts 43, 43 and the ball screw shaft 44 in a manner such that the optical diameter measurement assembly 50 is capable of shifting along the guide shafts 43, 43. More particularly describing, the optical diameter measurement assembly 50 has a plate 53 equipped with sliders 51, 51, which are adapted to slide on the guide shafts 44, 44, and with a nut 52, which is threadably penetrated by the ball screw shaft 44, so that that as the ball screw shaft 44 turns, the optical diameter measurement assembly 50 is caused to shift in the direction normal to the plane of the sheet of FIG. 2.

The ball screw shaft 44 has its end portions journalled in the support plates 41 and 42 by means of bearings, not shown, and the right end, as viewed in FIG. 1, of the ball screw shaft 44 extends beyond the support plate 42 and is connected via a coupling 61 to the output shaft of a pulse motor 60 supported by the support plate 42. A belt pulley 45 having the same working diameter as the pulley 16 is fixed about the right end portion of the ball screw shaft 44 at a location between the coupling 61 and the support plate 42. The other end of the ball screw shaft 44 extends beyond the support plate 41 and is connected to an encoder 70 supported by the support plate 41.

An idle pulley 46, shown in FIG. 2, is supported by the support plate 42 in a manner such that the idle pulley 46 can freely rotate in the support plate 42. A timing belt 47 is wound round the idle pulley 46 and the pulleys 16 and 45, and is given a certain amount of tension by means of a tension pulley 48 which turns as the timing belt 47 runs.

Incidentally, the support plates 41, 42, the guide shafts 43, 43, the ball screw shaft 44, the pulse motor 60, the encoder 70, etc. are enclosed in a cover 49. The screw pitches of the ball screw shafts 5 and 44 are the same.

An arm 54, extending horizontally over the single crystal ingot W, is provided on top of the plate 53 of the optical diameter measurement assembly 50, and the image sensor 55 with its photo sensitive means exposed and looking downward is provided at the fore end of the arm 54 in a manner such that the altitude of the image sensor 55 can be freely adjusted. Incidentally, this image sensor 55 is housed in a cover 56 of the optical diameter measurement assembly 50 which 56 has an opening in its bottom.

Figure 3:
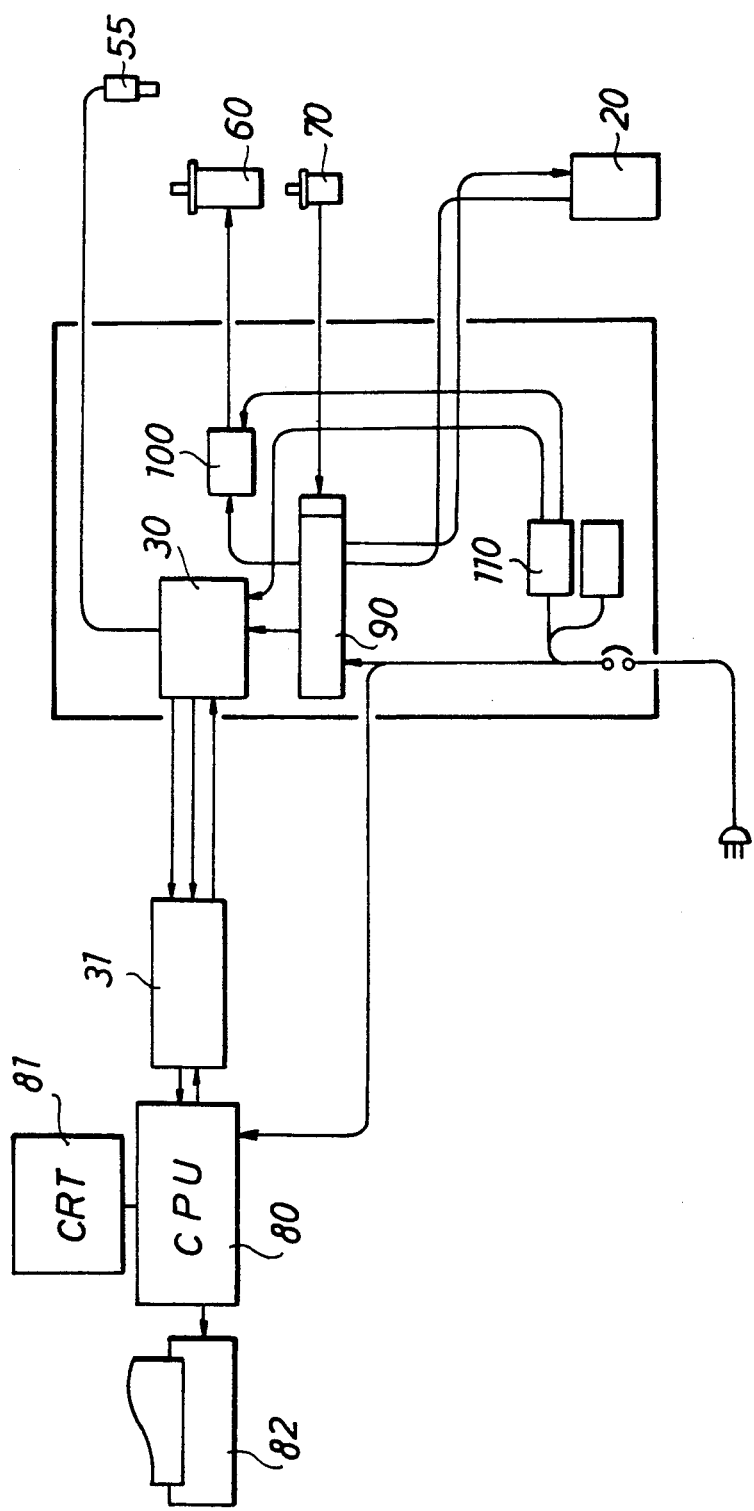
FIG. 3 is a block diagram showing the construction of the same apparatus.

As shown in FIG. 3, the image sensor 55 is electrically connected to the controller 30 (ref. FIG. 1), which controls the measuring behavior of the image sensor 55. The controller 30 is connected by way of an interface 31 to a central processing unit (hereinafter referred to as "CPU") 80, and also directly connected to a sequencer 90. To the CPU 80 are connected a CRT display 81 for displaying measurement data and a printer 82 for outputting the measurement data.

The sequencer 90 is connected to the operation panel 20 (ref. FIG. 1), and to the sequencer 90 are connected the encoder 70 (ref. FIG. 1) and a motor driver 100. Connected to the motor driver 100 is the pulse motor 60. Incidentally, in FIG. 3, the reference numeral 110 designates an AC power source for supplying electricity to the controller 30, the CPU 80, and the motor driver 100.

Next, the operation of the non-contact type automatic multi-point diameter measurement apparatus of this embodiment of the invention will be described.

In response to a command signal supplied from the sequencer 90, the motor driver 100 is energized and causes the pulse motor 60 to start turning, whereupon the ball screw shaft 44 connected to the pulse motor 60 starts rotating and, in synchronism with this, the torque of the pulse motor 60 is transmitted, via the pulley 45, the timing belt 47 and the pulley 16, to the other ball screw shaft 5 to make the ball screw shaft 5 to rotate. As the two ball screw shafts 5 and 44 rotate simultaneously in the same direction, the slider 11 and the nut 52, which are threadably engaged with the respective screw shaft, start shifting in the axial direction of the single crystal ingot W, whereby the light emission assembly 10 and the optical diameter measurement assembly 50 shift in the same direction. Now, since the working diameters of the pulleys 16 and 45 are identical, as stated above, the two ball screw shafts 5 and 44 rotate at the same rotational speed and also, since the screw pitches of the two ball screw shafts 5 and 44 are identical, the shift amount of the light emission assembly 10 is always equal to that of the optical diameter measurement assembly 50. Therefore, the light emission assembly 10 and the optical diameter measurement assembly 50 move as if they were of one body.

The shift amount of the light emission assembly 10 and the optical diameter measurement assembly 50 is computed from the number of revolution of the ball screw shaft 44 detected by the encoder 70, and each time the shift amount of the light emission assembly 10 and the optical diameter measurement assembly 50 amounts to any of predetermined values, that is, each time the light emission assembly 10 and the optical diameter measurement assembly 50 arrive at any of predetermined measurement points arranged along the axis of the single crystal ingot W, the encoder 70 outputs a measurement timing signal to the sequencer 90, whereupon the sequencer 90 outputs a measurement command signal to the controller 30. The controller 30 then supplies the image sensor 55 with a measurement command signal, and the image sensor 55 senses the light L emitted by the high-frequency fluorescent lamp 13 of the light emission assembly 10 laid below the single crystal ingot W, and detects the image of that region of the light L which is intercepted by the single crystal ingot W, and the image sensor 55 outputs a detection signal to the CPU 80 by way of the controller 30 and the interface 31.

Based on the detection signal received from the image sensor 55, the CPU 80 computes the length of that region of the light L which is identical to the diameter of the single crystal ingot W, and the value of this length is stored as the actually measured diameter D. Incidentally, if need be, this actually measured diameter value D can be displayed on the CRT display 81, or printed out by the printer 82.

By repeating this operation described above at different predetermined measurement points along the axis of the single crystal ingot W, it is possible to measure the diameter of the single crystal ingot W at a plurality of measurement points in a real time manner; and since these actually measured diameter data are free of the errors ascribable to human measurer's inclination, these values are reliable and more accurate.

Also, since the number of the points along the axis of the single crystal ingot W at which the diameter measurement is carried out can be arbitrarily determined, it is possible to obtain necessary and sufficient amount of actually measured diameter data, and it is also possible to minutely compare the sensor-detected diameter data obtained by the image sensor of the single crystal pulling apparatus with the actually measured diameter data, as the reference data, which latter are stored in the CPU 80 and printed out by the printer 81. As a result, it becomes possible to conduct a reliable adjustment of the accuracy of the image sensor of the single crystal pulling apparatus, and, hence, it is now possible to attain high precision controlling of the diameter of the single crystal ingot grown in the single crystal pulling apparatus. Incidentally, by connecting the CPU 80 of the non-contact type automatic multi-point diameter measurement apparatus of the present invention with the CPU of the single crystal pulling apparatus, it is possible to automatize the entire operations from the measurement of the diameters of the single crystal ingot W to the corrective adjustment of the image sensor of the single crystal pulling apparatus.

In the above embodiment, the apparatus of the present invention is applied to the measurement of the diameters of a single crystal ingot W, but it is of course possible to apply the same or similar apparatus within the scope of the invention to measurement of the diameters of any cylindrical bodies. Also, it is possible to employ a source of laser beam in place of the high-frequency fluorescent lamp.

It is further understood by those skilled in the art that the foregoing description is a preferred embodiment of the disclosed device and that various changes and modifications may be made in the invention without departing from the spirit and scope thereof.

What is claimed is:

1. A non-contact type automatic multi-point diameter measurement apparatus for measuring the diameter of a cylindrical body at different locations along its length in real-time manner without physically coming in contact with the cylindrical body, comprising:
   a movable elongated light emitting means having a length substantially greater than the general diameter of the cylindrical body and supported to move in the direction of an axis of the cylindrical body which is generally normal to a lengthwise axis of the light emitting means;
   a movable optical diameter measurement means facing the light emitting means across the cylindrical body, supported to move together with the light emitting means so as to always look toward the light emitting means across the cylindrical body, located at such a predetermined position relative to the light emitting means and the cylindrical body that at least the light emitted from both ends of the light emitting means can reach the optical diameter measurement means without being intercepted by the cylindrical body, and adapted to optically measure a diameter of the cylindrical body and output a signal indicative of the result of the diameter measurement;

means for moving said light emitting means and said optical diameter measurement means together to a plurality of predetermined positions with respect to a longitudinal direction of the cylindrical body;

a position detection means for detecting whether the optical diameter measurement means is in one of predetermined positions, and outputting a detection signal when it is detected that the optical diameter measurement means is in one of the predetermined positions;

a control means for actuating the optical diameter measurement means to measure a diameter of the cylindrical body in response to the detection signal received from the position detection means; and a data processing means for calculating a representative value of the diameter based on a measurement result signal received from the optical diameter measurement means, and for processing resulting data.

2. A non-contact type automatic multi-point diameter measurement apparatus as claimed in claim 1, wherein the elongated light emitting means is covered with a cover means having a slit extending along the length of the light emitting means which slit is substantially longer than the general diameter of the cylindrical body, and the optical diameter measurement means is located at such a predetermined position relative to the slit and the cylindrical body that at least the light emitted through both end portions of the slit can reach the optical diameter measurement means without being intercepted by the cylindrical body.

3. A non-contact type automatic multi-point diameter measurement apparatus as claimed in claim 1, wherein the optical diameter measurement means includes an image sensor.

4. A non-contact type automatic multi-point diameter measurement apparatus as claimed in claim 1, wherein the light emitting means comprises a high-frequency fluorescent lamp.

5. A method for performing real-time measurements of the diameter of a cylindrical body at different locations along its length without physical contact therewith, comprising the steps of:

moving an elongated light emitting means having a length substantially greater than the general diameter of the cylindrical body along the direction of an axis of the cylindrical body which is generally normal to a lengthwise axis of the light emitting means;

moving an optical diameter measurement means facing the light emitting means across the cylindrical body together with the light emitting means so as to always look toward the light emitting means across the cylindrical body, the optical diameter measurement means being located at such a predetermined position relative to the light emitting means and the cylindrical body that at least the light emitted from both ends of the light emitting means can reach the optical diameter measurement means without being intercepted by the cylindrical body to enable optical measurement of a diameter of the cylindrical body and output of a signal indicative of the measured diameter;

moving said light emitting means and said optical diameter measurement means together to a plurality of predetermined positions with respect to said axis of the cylindrical body;

detecting when the optical diameter measurement means is in one of a plurality of predetermined positions and outputting a corresponding detection signal;

actuating the optical diameter measurement means to measure a diameter of the cylindrical body and generate a measurement result signal in response to the detection signal received from the position detection means; and calculating a representative value of the diameter based on the measurement result signal.

6. The method according to claim 5, comprising the further step of:

repeating the diameter measurements at a plurality of predetermined positions longitudinally of the cylindrical body; and processing data corresponding to said measurements to generate a detailed printed record thereof.

* * * * *